(12) United States Patent
Lee (10) Patent No.: US 9,474,893 B2
(45) Date of Patent: Oct. 25, 2016

(54) TIP STRUCTURE FOR A SKIN CARE APPARATUS

(71) Applicant: Eunsung Global Corporation, Seoul (KR)

(72) Inventor: Ki Se Lee, Seoul (KR)

(73) Assignees: EUNSUNG GLOBAL CORPORATION, Seoul (KR); Ki Se Lee, Seoul (KR)

( * ) Notice: Subject to any disclaimer, the term of this patent is extended or adjusted under 35 U.S.C. 154(b) by 0 days.

(21) Appl. No.: 14/219,742

(22) Filed: Mar. 19, 2014

(65) Prior Publication Data
US 2014/0288622 A1 Sep. 25, 2014

(30) Foreign Application Priority Data
Mar. 22, 2013 (KR) ........................ 10-2013-0030892

(51) Int. Cl.
| | | |
|---|---|---|
| A61N 5/00 | (2006.01) | |
| A61N 1/04 | (2006.01) | |
| A61N 1/06 | (2006.01) | |
| A61N 1/32 | (2006.01) | |

(52) U.S. Cl.
CPC ............... *A61N 1/0476* (2013.01); *A61N 1/06* (2013.01); *A61N 1/328* (2013.01)

(58) Field of Classification Search
CPC ........ A61N 1/06; A61N 1/328; A61N 1/322; A61N 1/0476; A61B 2018/00452
USPC ......................................................... 607/99
See application file for complete search history.

(56) References Cited

U.S. PATENT DOCUMENTS

| | | | |
|---|---|---|---|
| 4,532,924 A * | 8/1985 | Auth et al. ...................... 606/50 |
| 5,257,635 A * | 11/1993 | Langberg ...................... 607/122 |
| 6,268,580 B1 * | 7/2001 | Boyer, Jr. .................. 219/69.15 |
| 6,283,961 B1 * | 9/2001 | Underwood et al. ........... 606/41 |
| 6,413,255 B1 * | 7/2002 | Stern ................................. 606/41 |
| 6,461,357 B1 * | 10/2002 | Sharkey et al. ................ 606/45 |
| 6,468,274 B1 * | 10/2002 | Alleyne ............ A61B 18/1206 604/114 |
| 6,592,580 B1 * | 7/2003 | Stockert .......................... 606/41 |
| 6,714,823 B1 * | 3/2004 | De Lurgio et al. ........... 607/122 |
| 7,267,675 B2 * | 9/2007 | Stern et al. ...................... 606/41 |
| 7,473,251 B2 * | 1/2009 | Knowlton et al. .............. 606/41 |
| 7,686,802 B2 * | 3/2010 | Stevens-Wright .............. 606/41 |
| 7,715,921 B2 * | 5/2010 | Palti .............................. 607/115 |
| 8,394,088 B2 * | 3/2013 | West, Jr. ......................... 606/37 |
| 8,406,894 B2 * | 3/2013 | Johnson et al. ............. 607/101 |
| 8,515,553 B2 * | 8/2013 | Schenck ....................... 607/100 |
| 2001/0037118 A1 * | 11/2001 | Shadduck ..................... 606/131 |
| 2002/0016601 A1 * | 2/2002 | Shadduck ..................... 606/131 |

(Continued)

FOREIGN PATENT DOCUMENTS

KR 10-1065611 B1 9/2011

*Primary Examiner* — Kaitlyn Smith
*Assistant Examiner* — Yasamin Ekrami
(74) *Attorney, Agent, or Firm* — Rabin & Berdo, P.C.

(57) ABSTRACT

Disclosed therein is a tip structure for a skin care apparatus. The tip structure includes a first electrode formed on a substrate mounted on the front end part of a tip case and a second electrode formed on the periphery of the front end part of the tip case so as to provide a wide electrode area. The tip structure for the skin care apparatus, which supplies high frequency energy to the skin through electrodes formed at the front end portion of the tip case, includes: a first electrode formed on the substrate mounted on the front end part of the tip case; and a second electrode formed on a peripheral portion of the front end part of the tip case.

4 Claims, 8 Drawing Sheets

(56) References Cited

U.S. PATENT DOCUMENTS

| | | | |
|---|---|---|---|
| 2004/0193150 A1* | 9/2004 | Sharkey | A61B 18/1402 606/41 |
| 2004/0199226 A1* | 10/2004 | Shadduck | 607/96 |
| 2006/0095032 A1* | 5/2006 | Jackson et al. | 606/41 |
| 2007/0088413 A1* | 4/2007 | Weber et al. | 607/99 |
| 2008/0077129 A1* | 3/2008 | Van Wyk et al. | 606/46 |
| 2008/0200969 A1* | 8/2008 | Weber | 607/102 |
| 2009/0018628 A1* | 1/2009 | Burns et al. | 607/101 |
| 2009/0043247 A1* | 2/2009 | Kreindel et al. | 604/21 |
| 2009/0093749 A1* | 4/2009 | Shalev et al. | 604/20 |
| 2010/0016854 A1* | 1/2010 | Carmel | A61B 18/148 606/48 |
| 2010/0179531 A1* | 7/2010 | Nebrigic et al. | 606/33 |
| 2011/0028816 A1* | 2/2011 | Simpson | A61B 5/14532 600/345 |
| 2012/0078289 A1* | 3/2012 | Livneh | 606/205 |
| 2014/0128944 A1* | 5/2014 | Stern et al. | 607/101 |

* cited by examiner

TIP STRUCTURE FOR A SKIN CARE APPARATUS

BACKGROUND OF THE INVENTION

1. Field of the Invention

The present invention relates to a skin care apparatus, and more particularly, to a tip structure for a skin care apparatus, which includes a first electrode and a second electrode formed on a body of a tip which transmits high frequencies to the skin so as to form a wide contact area of the first electrode and the second electrode.

2. Background Art

For skin care and reproduction, there is a non-invasive method that is effective in promoting regrowth of collagen.

The non-invasive method is to promote formation of collagen by temperature of the dermis layer elevated by RF high frequencies irradiated to the skin, and in this instance, high frequencies are irradiated to the skin using a tip having unipolar or bipolar electrodes.

Figure 1:
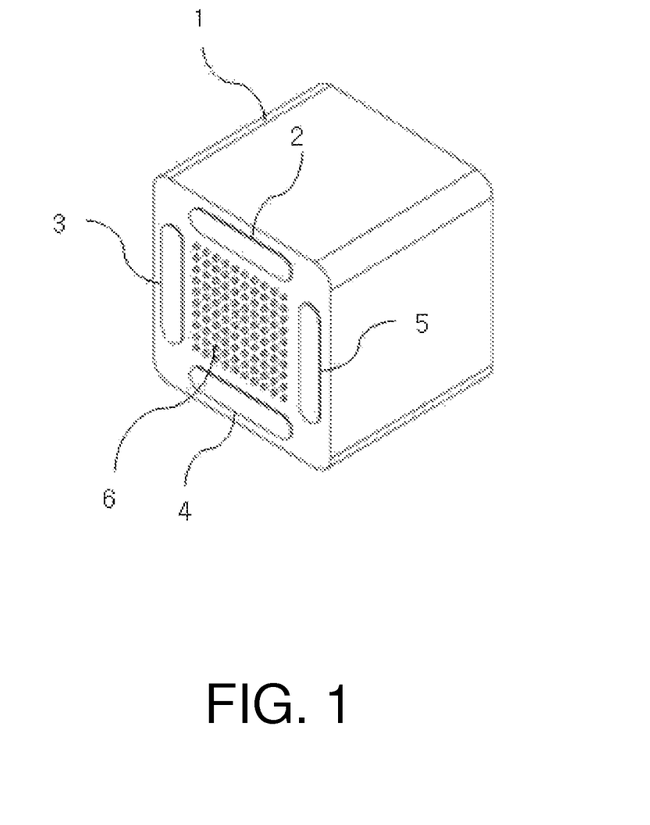
FIG. 1 is a view showing a tip structure of a conventional skin care apparatus.

Korean Patent No. 10-1065651 discloses such a tip. As shown in FIG. 1, the conventional tip includes a body 1, a plurality of positive electrodes 6 mounted on the front end surface of the front part of the body 1, and a plurality of negative electrodes 2, 3, 4 and 5 mounted along the outer peripheries of the positive electrodes 6, and the plural positive electrodes are arranged on one PCB at regular intervals in a lattice form.

Therefore, high frequencies flow between the positive electrodes 6 and the negative electrodes 2, 3, 4 and 5 through the skin so as to supply high frequencies to the dermis layer.

However, because the positive electrodes 6 and the negative electrodes 2, 3, 4 and 5 are densely formed on the front end portion of the body 1 which is a limited area so as to form a narrow contact area of the electrodes, when the tip is not in close contact with the skin but is partly in contact with the skin, electric currents are concentrated just on the contact area, such that the skin tissue may be damaged due to excessive electric currents.

SUMMARY OF THE INVENTION

Accordingly, the present invention has been made to solve the above-mentioned problems occurring in the prior arts, and it is an object of the present invention to provide a tip structure for a skin care apparatus, which includes: a PCB mounted on a front end part of a tip case; a first electrode formed on a substrate such as an FPCB or on an electric conductor; and a second electrode formed on a peripheral portion of the front end of the tip case so as to provide a wide electrode area.

To accomplish the above object, according to the present invention, there is provided a tip structure for a skin care apparatus to supply high frequency energy to the skin through electrodes which are formed on a substrate mounted at a front end part of a tip case, including: a first electrode formed on the substrate mounted on the front end part of the tip case; and a second electrode extending from a peripheral portion of the front end part of the tip case to the outer face.

According to the preferred embodiment of the present invention, the tip for the skin care apparatus includes the substrate having the second electrode formed on the tip case and the first electrode formed on the front end of the tip case, such that a wide electrode area is formed even though the size of the tip is the same as the conventional tip, thereby increasing a contact area to the skin so as to smoothly supply high frequencies to the skin without concentration of electric currents.

BRIEF DESCRIPTION OF THE DRAWINGS

The above and other objects, features and advantages of the present invention will be apparent from the following detailed description of the preferred embodiment of the present invention in conjunction with the accompanying drawings, in which.

DETAILED DESCRIPTION OF THE PREFERRED EMBODIMENT

Reference will be now made in detail to the preferred embodiments of the present invention with reference to the attached drawings.

Figure 2:
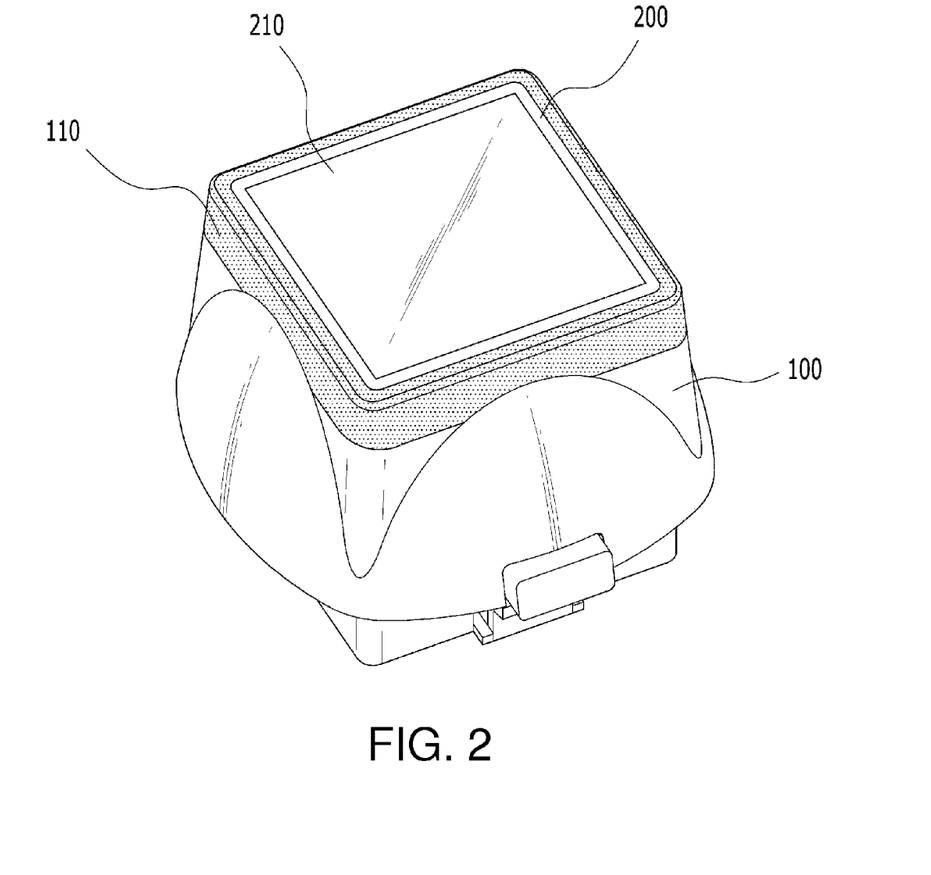
FIG. 2 is a view showing a tip structure for a skin care apparatus according to a first preferred embodiment of the present invention.

FIG. 2 illustrates an external structure of a tip for a skin care apparatus according to a preferred embodiment of the present invention. In FIG. 2, a substrate 200 is mounted on a front end part of a tip case 100 which is an insulator made with plastic, and has a first electrode 210. A second electrode 110 is formed on the outer periphery of the front end part of the tip case 100, namely, on the edge portion of the tip case 100 on which the substrate 200 is seated, by plating.

In this instance, the substrate 200 may be a PCB, an FPCB, or others, and the first electrode 210 is mounted on an area except the edge periphery of the substrate 200 so as to be spaced apart from the second electrode 110 disposed on the tip case 100, such that the first electrode 210 is insulated by the edge portion of the substrate 200.

The second electrode 110 extends to the external portion of the front part of the tip case 100 so as to have a wide and stable contact area.

Figure 3:
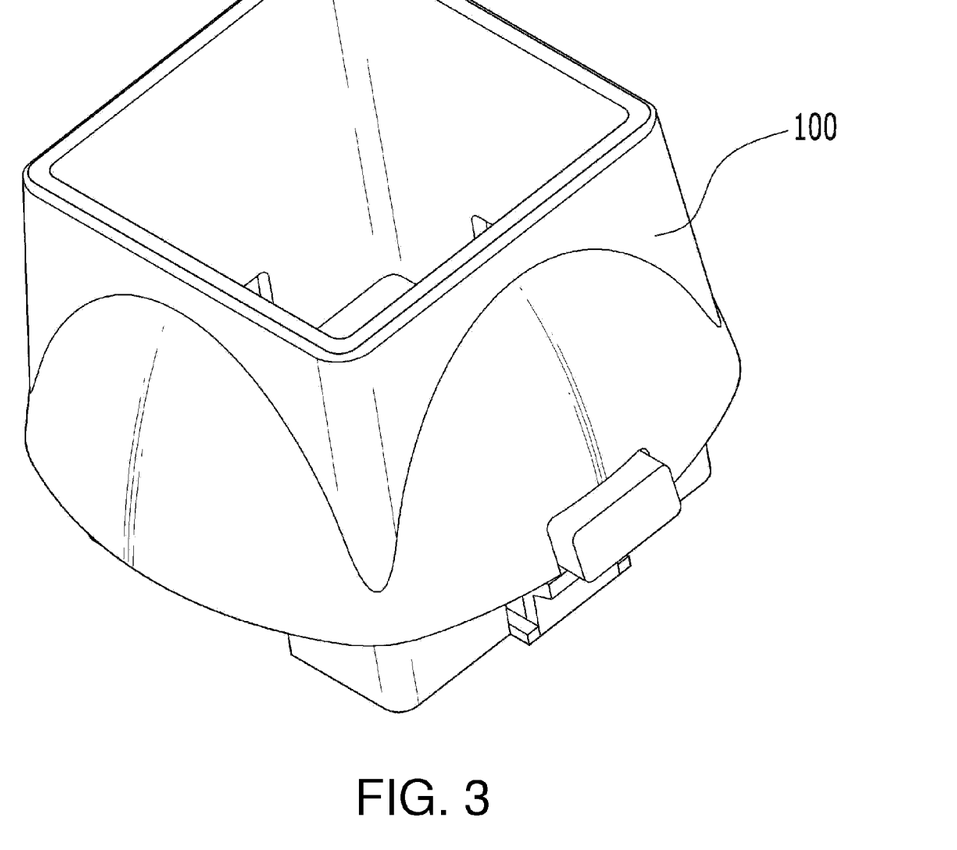
FIG. 3 is a view showing the form of a tip case.
Figure 4:
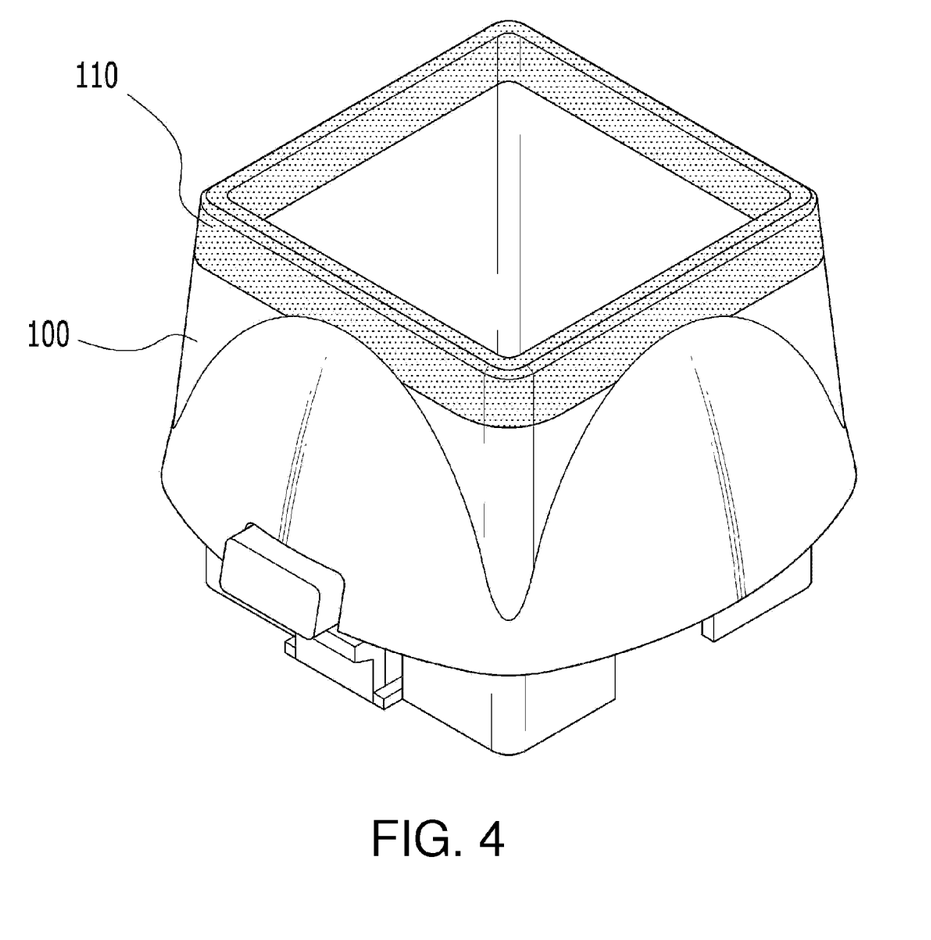
FIG. 4 is a view showing the form of the tip case on which a second electrode is formed.

FIG. 3 illustrates a form of the tip case 100 in a state where the substrate 200 is not yet mounted and the tip case 100 is not yet plated. The substrate 200 is a product made by plastic injection molding. Before the substrate 200 is mounted on the tip case 100, as shown in FIG. 4, when the front end part of the tip case 100, namely, a part where the second electrode 100 will be formed, is deposited in a plating solution, the front end part, the inner face and the outer face of the tip case are plated, and thus, the second electrode 110 is formed.

After that, as shown in FIG. 2, the substrate 200 on which the first electrode 210 is formed is fixedly seated on the tip case 100 on which the second electrode 110 is formed, such that the tip for the skin care apparatus is finished.

In this instance, the substrate 200 is in the form of a plate has the first electrode 210 formed on the upper surface thereof and a connection terminal disposed on a lower surface so as to be electrically connected with the second electrode 110 formed on the tip case 100, so that the first electrode 210 and the second electrode 110 can be respectively connected with terminals by just one substrate.

Figure 5:
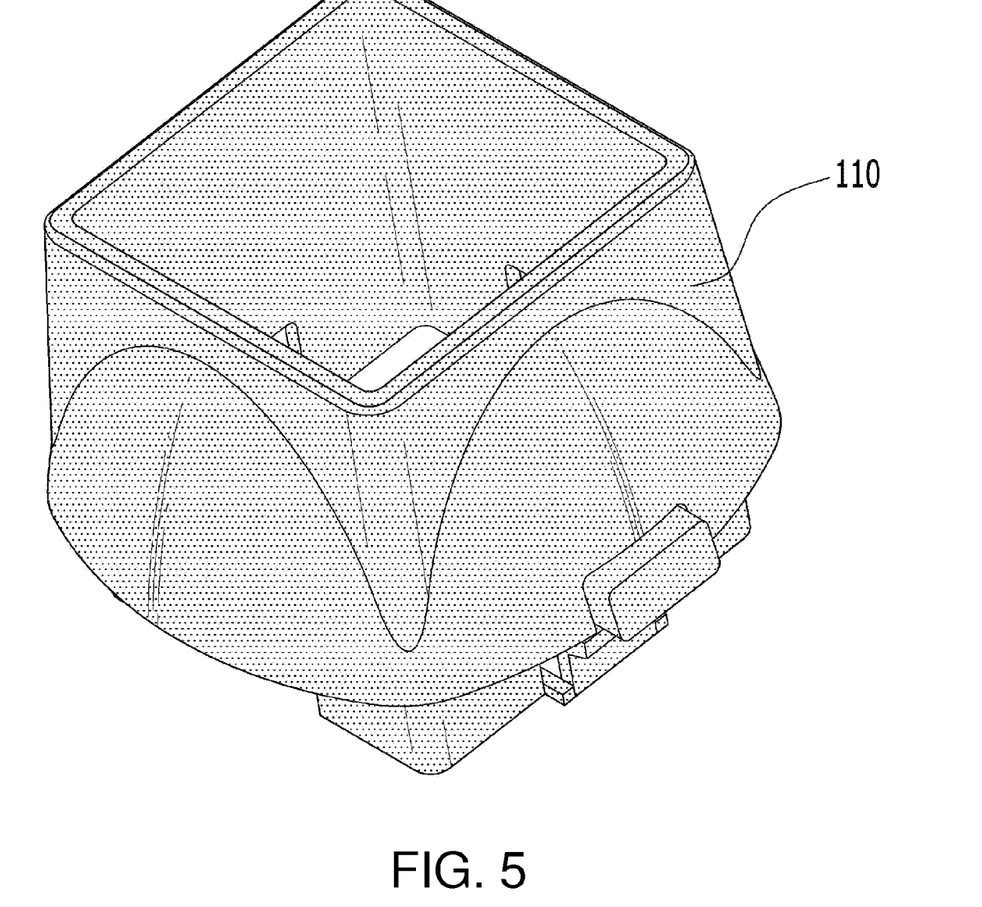
FIG. 5 is a view showing a tip structure according to a second preferred embodiment of the present invention.

In the meantime, FIG. 5 illustrates a tip structure for a skin care apparatus according to a second preferred embodiment of the present invention, wherein the tip case 100 is completely deposited in the plating solution such that the inner face and the outer face of the tip case 100 are all plated. Because the second electrode 110 is formed on the entire surface of the tip case 100, the tip has a wide and stable contact area.

Figure 6:
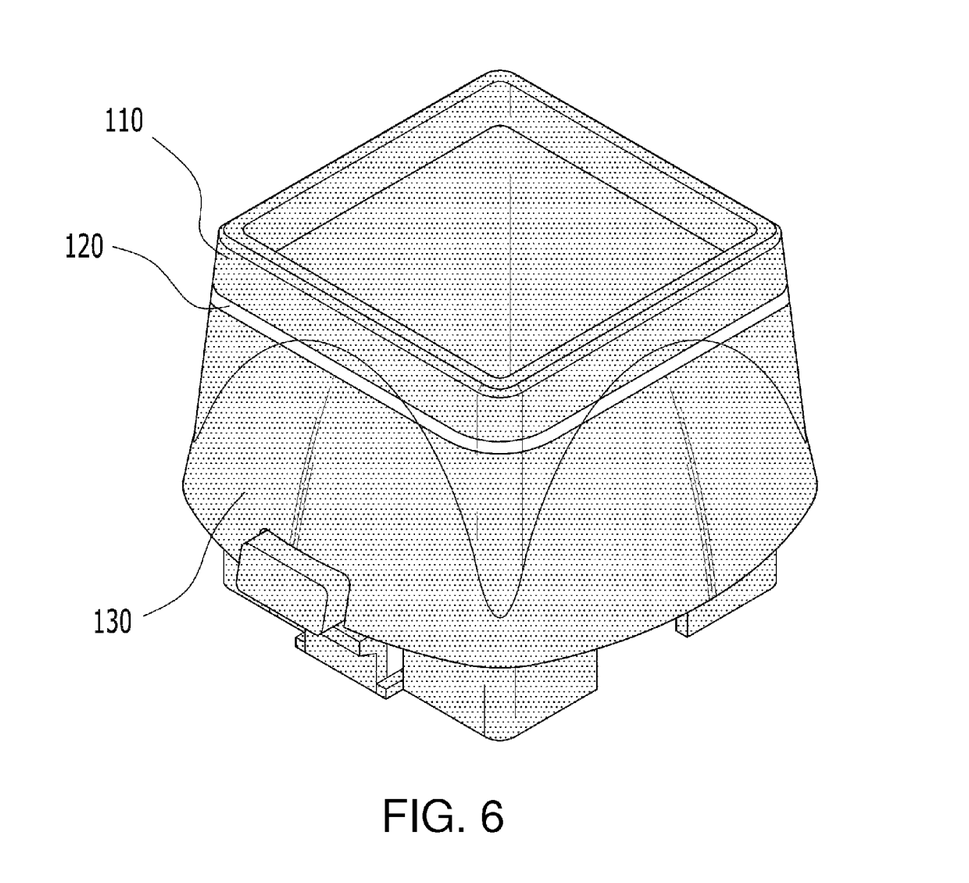
FIG. 6 is a view showing a tip structure according to a third preferred embodiment of the present invention.

FIG. 6 illustrates a tip structure for a skin care apparatus according to a third preferred embodiment of the present invention. Like FIG. 5, the entire surface of the tip case 100 is plated. The tip case 100 is divided into a front portion which will be used as the second electrode 110 and a rear portion 130 which will not be used as the second electrode, and includes a boundary portion 120 formed between the front portion which will be used as the second electrode 110 and the rear portion 130 which will not be used as the second electrode, such that the front portion and the rear portion are insulated from each other and are not electrically connected.

The boundary portion 120 may be formed when the plating of the boundary portion 120 is removed by laser machining or mechanical machining.

Alternatively, the tip case 100 may be formed by double shot injection. That is, the portion where the second electrode 110 will be formed is injection-molded by resin for plating, and the rear portion 130 is injection-molded by uncoated resin, such that just the portion where the second electrode 110 will be formed has conductivity by plating.

In such a case, just the front portion of the boundary portion 120 is used as the second electrode 110 so as to form an area corresponding to the first electrode 210 to supply stable high frequencies. The rear portion 130 is not used as the second electrode, but because it is plated, it may provide a beautiful appearance rather than the case that the portion injection-molded with plastic is exposed.

Figure 7:
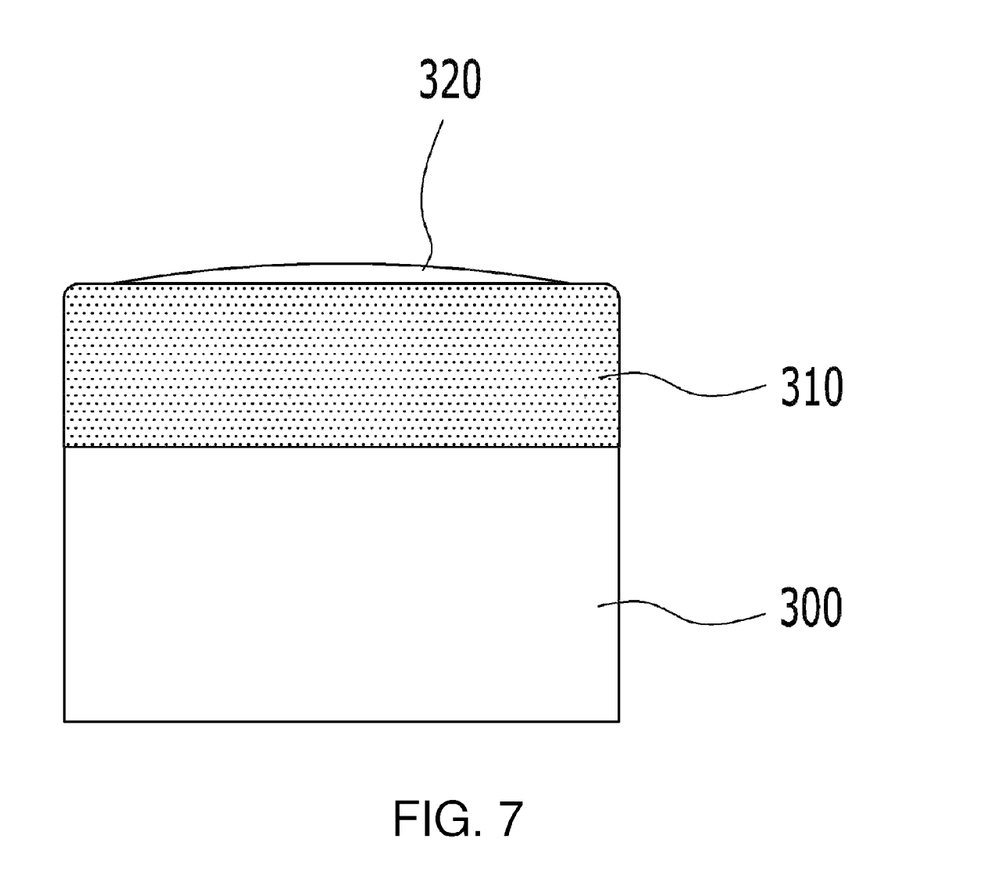
FIGS. 7 and 8 are views showing a tip structure according to a fourth preferred embodiment of the present invention.
Figure 8:
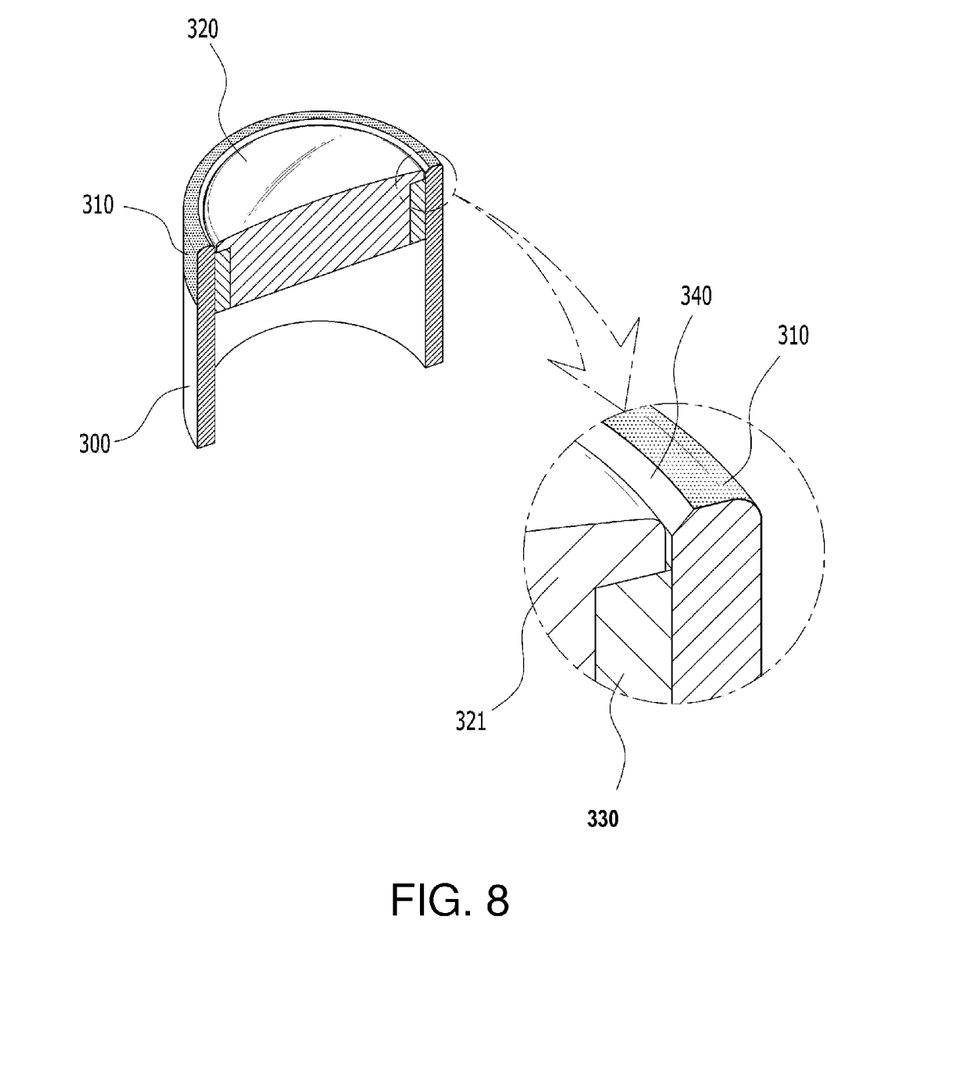

FIGS. 7 and 8 illustrate a tip structure for a skin care apparatus according to a fourth preferred embodiment of the present invention. In FIGS. 7 and 8, the tip includes: a second electrode 310 formed on the outer part including the outer periphery of the front end part of a tip case 300 of a hollow cylindrical shape by plating; a first electrode 320 made of a hard material and mounted on the tip case 300, the first electrode 320 having a cylindrical body and a dome-shaped or convexly curved upper face; a stepped-jaw portion 330 formed along the inner circumference of the tip case 300; and a protrusion 321 protruding outwardly along the outer circumference of the first electrode 320. While the first electrode 320 is inserted to the inside from the top of the tip case 300, the protrusion 321 is caught and seated onto the stepped-jaw portion 330.

In this instance, the dome-shaped or convexly curved upper surface of the first electrode 320 is seated in such a way as to protrude over the front end of the tip case 300. The first electrode 320 has a size that there is a gap 340 between the outer circumference of the first electrode 320 and the inner circumference of the tip case 300, and the gap 340 is maintained by the stepped-jaw portion 330.

That is, the protruding width of the protrusion 321 is wider than the protruding width of the stepped-jaw portion 330, such that the first electrode 320 and the portion of the tip case 300 where the second electrode 310 is formed are spaced apart from each other by the gap 340 so as to keep an insulated state, and if necessary, the gap 340 may be filled with insulating material.

Moreover, the second electrode 320 may be made of a metal material having conductivity or may be an electrode having conductivity by plating applied on the outer surface of a substrate made of a plastic material.

Furthermore, the first electrode 320 has a coated layer formed on the upper surface thereof by being coated with vinyl or resin, so that the first electrode 320 is not in direct contact with the skin but is in indirect contact with the skin through the coated layer so as to protect the skin.

Additionally, the second electrode 310 may be formed by the various preferred embodiments described above.

What is claimed is:

1. A tip structure for a skin care apparatus to supply high frequency energy to a skin, the tip structure for the skin care apparatus comprising:

a tip case in a hollow tube shape having a wall defining and surrounding an empty inside space, wherein the wall includes an inner face that faces the empty inside space of the tip case, an outer face opposite to the inner face, and a top rim part connecting the inner face and the outer face;

a substrate mounted on the top rim part of the wall, the substrate being surrounded by an outer periphery of the top rim part;

a first electrode formed on an area of the substrate except an edge periphery of the substrate, the first electrode being surrounded by the outer periphery of the top rim part without being extended to the outer face; and a second electrode coated on the inner face, the top rim part and the outer face of the wall without discontinuity, wherein the second electrode is apart from the first electrode with the edge periphery of the substrate being disposed therebetween, wherein a to surface of the first electrode, a top surface of the substrate and a top surface of the second electrode are disposed substantially at a same level with each other, wherein an outermost peripheral surface of the substrate is covered by the inner face of the wall of the tip case, and wherein the wall of the tip case is a supporting frame of the tip structure that supports the tip structure, and the second electrode disposed on the inner face of the wall is a coated layer which does not work as a supporting frame.

2. The tip structure according to claim 1, wherein the second electrode is formed by plating.

3. A tip structure for a skin care apparatus to supply high frequency energy to a skin, the tip structure for the skin care apparatus comprising:

a tip case in a hollow tube shape that has a wall defining and surrounding an empty inside space, wherein the wall includes an inner face that faces the empty inside space of the tip case, an outer face opposite to the inner face, and a top rim part connecting the inner face and the outer face, the tip case further including a stepped-jaw portion on the inner face of the wall, the stepped-jaw portion including an inner surface that faces the empty inside space of the tip case, an outer surface in contact with the inner face of the wall and a top surface connecting the inner and outer surfaces of the stepped-jaw portion, the top surface of the stepped-jaw portion extending in a direction perpendicular to the inner surface of the stepped-jaw portion to be connected with the inner face of the wall;

a second electrode coated on the top rim part and the outer face of the wall, wherein the second electrode is not coated on the inner face of the wall; and a first electrode mounted inside the tip case and seated on the top surface of the stepped-jaw portion, the first electrode having a dome-shaped upper face protruding above the top rim part of the wall, the first electrode being electrically insulated from the second electrode by a gap formed between an outer circumference of the first electrode and an inner circumference of the tip case, wherein no material is filled in the gap, wherein the first electrode has a protrusion formed on an outer circumference thereof seated on the top surface of the stepped-jaw portion, and an outer periphery of the first electrode below the protrusion of the first electrode is in contact with the inner surface of the stepped-jaw portion, and a base of the protrusion is directly seated on and in direct contact with the top surface of the stepped-jaw portion, wherein a thickness of the stepped-jaw portion in a radial direction is greater than a length of the protrusion of the first electrode in the radial direction, such that the gap is formed between the first electrode and the tip case and that the protrusion of the first electrode, taken from a plan view, is disposed entirely within the thickness of the stepped-jaw portion.

4. The tip structure according to claim 3, wherein the first electrode is made of a metal material having conductivity.

* * * * *